Figure 1A:
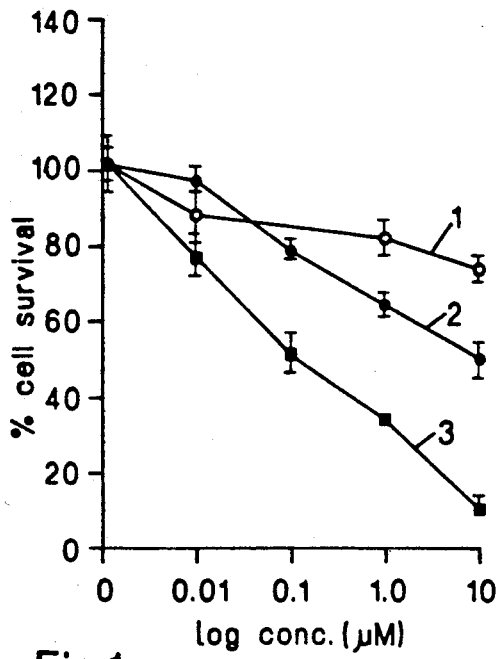
Figure 1B:
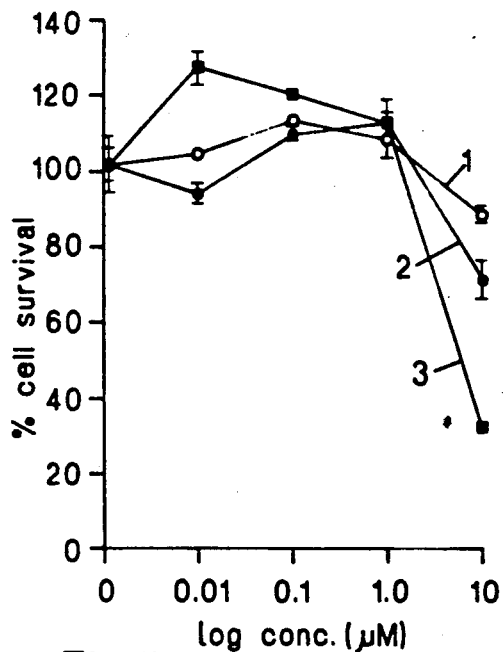
Figure 1C:
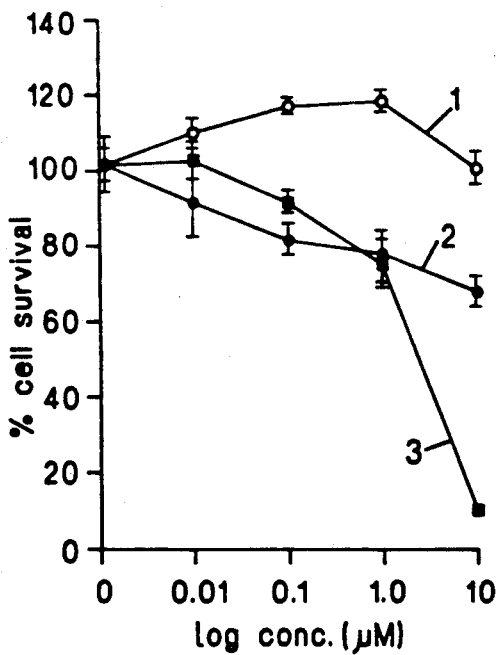
Figure 1D:
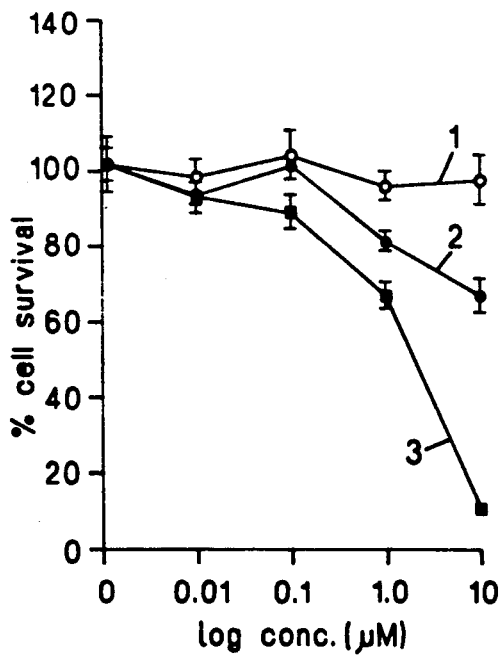

United States Patent [19]

Patterson

[11] Patent Number: 5,132,327
[45] Date of Patent: Jul. 21, 1992

[54] ANTI-CANCER COMPOUNDS

[75] Inventor: Laurence H. Patterson, Glenfield, England

[73] Assignee: National Research Development Corporation, London, England

[21] Appl. No.: 674,354

[22] PCT Filed: Oct. 12, 1990

[86] PCT No.: PCT/GB90/01574
  § 371 Date: Apr. 10, 1991
  § 102(e) Date: Apr. 10, 1991

[30] Foreign Application Priority Data

Oct. 13, 1989 [GB] United Kingdom ............... 8923075

[51] Int. Cl.$^5$ .................. C09B 1/16; C07C 97/21; A61K 31/13
[52] U.S. Cl. ................... 514/644; 552/236; 552/237; 552/238; 552/240; 552/243; 552/244; 552/247; 552/249; 552/255
[58] Field of Search ............. 552/243, 244, 247, 249, 552/238, 255, 236, 237, 240; 515/644

[56] References Cited

U.S. PATENT DOCUMENTS

| 3,174,994 | 3/1965 | Sutton ........................... 260/469 |
| 4,138,415 | 2/1979 | Murdock et al. ............... 260/378 |
| 4,197,249 | 4/1980 | Murdock et al. ............... 552/247 |
| 4,275,010 | 6/1981 | Murdock ........................ 552/243 |
| 4,278,605 | 7/1981 | Murdock ........................ 552/218 |
| 4,278,689 | 7/1981 | Murdock et al. ............... 514/656 |
| 4,430,501 | 2/1984 | Murdock et al. ............... 544/72 |
| 4,526,989 | 7/1985 | Murdock et al. ............... 549/316 |
| 4,540,519 | 9/1985 | Murdock et al. ............... 544/79 |
| 4,614,618 | 9/1986 | Murdock et al. ............... 552/247 |
| 4,686,218 | 8/1987 | Marinis et al. ................. 514/213 |
| 4,820,738 | 4/1989 | Murdock et al. ............... 514/656 |
| 4,963,554 | 10/1990 | Combs et al. .................. 514/259 |

FOREIGN PATENT DOCUMENTS

| 138302A | 4/1985 | European Pat. Off. ......... 552/243 |
| 145226A | 6/1985 | European Pat. Off. ......... 552/243 |
| 0145226 | 6/1985 | European Pat. Off. ......... 552/243 |
| 194218 | 3/1970 | Fed. Rep. of Germany . |
| 2036554A | 7/1980 | United Kingdom ............. 552/243 |
| 2036554 | 7/1980 | United Kingdom ............. 552/243 |

OTHER PUBLICATIONS

J. Het. Chem., 1969, 6, 389-392, Fujiwara et al., "N-Oxides and S-oxides of Ellipticine Analogues (1)".
  List continued on next page.

Primary Examiner—Marianne Cintins
Assistant Examiner—Kimberly J. Kestler
Attorney, Agent, or Firm—Nixon & Vanderhye

[57] ABSTRACT

Compounds of formula (I)

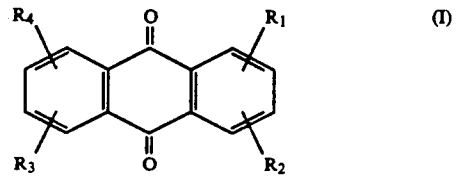

in which $R_1$, $R_2$, $R_3$ and $R_4$ are each separately selected from hydrogen, X, NH—A—NHR and NH—A—N(O)R'R" wherein X is hydroxy, halogeno, amino, $C_{1-4}$ alkoxy or $C_{2-8}$ alkanoyloxy, A is a $C_{2-4}$ alkylene group with a chain length between NH and NHR or N(O)R'R" of at least 2 carbon atoms and R, R' and R" are each separately selected from $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R" and R" are attached forms a heterocyclic group having 3 to 7 atoms in the ring, but with the proviso that at least one of $R_1$ to $R_4$ is a group NH—A—N(O)R'R", and physiologically acceptable salts thereof are of value in the treatment of cancer.

13 Claims, 1 Drawing Sheet

OTHER PUBLICATIONS

Tetrahedron, 1988, 44, 3627–3631, Langendoen et al., "An approach to novel ellipticine glycosides".

Tetrahedron, 1989, 45, 1759–1762, Langendoen et al., "Regiospecific C-9 substitution of ellipticine derivatives".

Phytochemistry, 1972, 11, 3073–3075, Bruneton et al., "Alcaloides des ecorces d'Ochrosia Vieillardii".

Helvetica Chimica Acta, 1967, 50, 1885–1892, Bild et al., "Notiz uber die massenspektren von N-oxiden".

Anti-Cancer Drug Design, 1986, 1, 259–268, Jarman et al., "Analogues of tamoxifen . . . ".

Int. J. Radiation Oncology Biol. Phys., 1986, 12, 1239–1242, Zeman et al., "SR-4233: A new bioreductive agent".

The Chemistry of Antitumor Agents, Wilman (ed.), 1990, 342–369, Jenkins, "Hypoxia-selective agents . . . ".

Science, 1974, 186, 647–648, Hulbert et al., "Hycanthone Analogs: . . . ".

Structure-Activity Relationship of Anti-Tumor Agents, Reinhoudt et al. (eds.) 1983, 47–57, Connary, "Alkylating Prodrugs in Cancer Chemotherapy".

J. Med. Chem., 1989, 24, 23–30, Katzhendler et al., "Synthesis of aminoanthraquinone derivatives . . . ".

J. Med. Chem., 1989, 32, 1724–1728, Stefanska et al., "Synthesis of . . . 1,4-bis[(aminoalkyl)amino]anthracene-9,10-diones . . . ".

Progress in Medicinal Chemistry, Ellis and West (eds.), 1983, 20, 83–118, Cheng et al., "The design, synthesis and development . . . anthraquinones".

ANTI-CANCER COMPOUNDS

This invention relates to novel anthraquinones which are of particular value in the treatment of cancer.

A wide variety of aminoalkylamino anthraquinones (aminoalkylaminoanthracene-9,10-diones) has been described for use as chemotherapeutic agents for the treatment of cancer, perhaps the most active being the compound mitoxantrone (mitozantrone) of formula

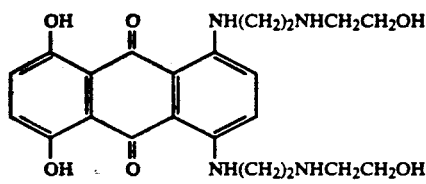

which is the subject of U.S. Pat. No. 4,197,249 and U.K. Patent 2,004,293B. However, in common with other cytotoxic chemotherapeutic agents the aminoalkylamino anthraquinones have the disadvantgage that their activity is not confined to neoplastic cells and they therefore exhibit various undesirable side effects including, to a greater or lesser extent among the different compounds, myelosuppression and cardiotoxicity.

It is an object of the present invention to provide a group of anthraquinone pro-drugs which are of lesser cytotoxicity than the drug itself, preferably being substantially non-cytotoxic, the pro-drugs being converted in vivo under the anaerobic conditions within neoplastic tissue to the cytotoxic drug thereby mitigating the side effects of administering that drug directly.

Accordingly the present invention comprises a compound of formula (I)

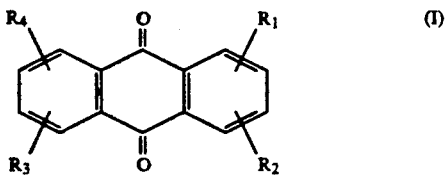

in which $R_1$, $R_2$, $R_3$ and $R_4$ are each separately selected from hydrogen, X, NH—A—NHR and NH—A—N(O)R'R" wherein X is hydroxy, halogeno amino, $C_{1-4}$ alkoxy or $C_{2-8}$ alkanoyloxy, A is a $C_{2-4}$ alkylene group with a chain length between NH and NHR or N(O)R'R" of at least 2 carbon atoms and R, R' and R" are each separately selected from $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, but with the proviso that at least one of $R_1$ to $R_4$ is a group NH—A—N(O)R'R", the compound optionally being in the form of a physiologically acceptable salt.

The compounds of formula (I) contain at least one substituent group NH—A—N(O) R'R" having the terminal, tertiary nitrogen atom in N-oxide form. Although groups of this type are not unknown, for example being described in European Patent Application A-0 145 226 as one of the various alternative forms of substituent in a group of substituted nitroacridones, it had not previously been appreciated that such a substituent confers valuable properties as compared with the compound containing the corresponding group NH—A—NR'R" in which the terminal, tertiary nitrogen atom is not in N-oxide form. Thus, such N-oxides are bioreductively activated within neoplastic tissue to form the cytotoxic compound containing an NH—A—NR'R" group thereby providing the desired anti-cancer activity of this compound but with mitigation of its undesired side effects.

It will be seen that in addition to the one or more substituents NH—A—N(O)R'R" in N-oxide form the compounds (I) may contain one or more substituents NH—A—NHR. Whilst these compounds, as compared with those containing no group NH—A—NHR, may exhibit some degree of cytotoxicity and are thus less preferred, this will nonetheless be at a lower level than the corresponding compound in which none of the aminoalkylamino groups is in N-oxide form and full cytotoxicity will only be expressed on conversion of the group(s) NH—A—N(O)R'R" to group(s) NH—A—NR'R".

As regards the groups NH—A—NHR and NH—A—N(O)R'R", A may be branched but is conveniently a straight chain alkylene group, i.e. tetramethylene, especially trimethylene, or particularly ethylene.

R, R' and R" may also have a branched carbon chain but are conveniently straight chain whether they are alkyl groups or hydroxy-substituted alkyl groups. When R, R' or R" is a monohydroxyalkyl group this is conveniently substituted terminally and when R, R' or R" is a dihydroxyalkyl group this is conveniently substituted terminally by one of the hydroxy groups. When R, R' and R" are alkyl the preference is for a group of three or especially two or one carbon atoms and when R, R' and R" are hydroxy-substituted alkyl the preference is for the alkyl group to be of three carbon atoms or, in the case of a monohydroxyalkyl group, alternatively of two carbon atoms. Examples of preferred individual groups R, R' and R" are $CH_3$, $CH_2CH_2CH_3$, $CH_2CH_2OH$, $CH_2CH_2CH_2OH$, $CH(CH_3)CH_2OH$, and $CH_2CHOHCH_2OH$ and especially $CH_2CH_3$. Whilst R' and R" will more usually be identical there can be certain advantages as described hereinafter in having non-identical groups R' and R".

Alternatively, as indicated, R' and R" together with the nitrogen atom to which they are attached may represent a heterocyclic group —$N(CH_2)_n$ where n is 2 to 6, i.e. aziridin-1-yl, azetidin-1-yl, pyrrolidin-1-yl, piperidin-1-yl and perhydroazepin-1-yl, the smaller groups such as azetidin-1-yl and especially aziridin-1-yl being of most interest.

Specific groups NH—A—NHR of particular interest are NH—$(CH_2)_2$—$NHCH_3$, NH—$(CH_2)_2$—$NHCH_2CH_2OH$, NH—$(CH_2)_2$—$NHCH(CH_3)CH_2OH$, NH—$(CH_2)_2$—$NHCH_2CHOHCH_2OH$, especially NH—$(CH_2)_2$—$NHCH_2CH_2OH$ and particularly NH—$(CH_2)_2$—$NHC_2H_5$, whilst specific groups NH—A—N(O)R'R" of particular interest are NH—$(CH_2)_2$—$N(O)(CH_3)C_2H_5$, NH—$(CH_2)_2$—$N(O)(CH_2CH_2OH)_2$, NH—$(CH_2)_2$—$N(O)(CH_2CH_2CH_2OH)_2$, NH—$(CH_2)_2$—$N(O)(CH(CH_3)CH_2OH)_2$, NH—$(CH_2)_2$—$N(O)(CH_2CHOHCH_2OH)_2$, especially NH—$(CH_2)_2$—$N(O)(CH_3)_2$ and particularly NH—$(CH_2)_2$—$N(O)(C_2H_5)_2$.

As regards the groups X, the halogeno groups are preferably bromo and especially chloro. Alkoxy and alkanoyloxy groups X may be branched or especially straight chain and are conveniently of 1 or 2 carbon atoms for the alkyl groups and of 2 or 3 carbon atoms for the alkanoyl groups. Examples of such groups X are therefore chloro, amino and especially methoxy, ethoxy, acetyl and propionyl. However hydroxy groups are preferred as the group or groups X.

Formula (II) illustrates the system used for numbering the various positions of the anthracene-9,10-dione ring system.

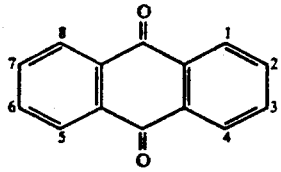

It will be seen from this formula that, due to the symmetrical nature of the molecule, certain substitution patterns are equivalent, for example 1,4 and 5,8. Preferences as to positions of substitution are expressed herein by identifying groups $R_1$ to $R_4$ which are other than hydrogen in the order $R_1$, $R_2$, $R_3$, $R_4$ and, as is conventional practice, by identifying substituted positions in the order 1. 2, 3, 4, 5, 6, 7, 8. Thus, for example, the compound having one substituent only at a ring position meta to an oxo group is identified as having that substituent as a group $R_1$ at position 1 and groups $R_2$, $R_3$ and $R_4$ which are hydrogen.

Any of positions 1, 2, 3, 4, 5, 6, 7 and 8 in the compound (I) may be substituted by a group NH—A—N(O)R'R" but positions 1, 4, 5 and 8 are of most interest for substitution by such a group and, indeed, also by the other substituent groups. At least one group NH—A—N(O)R'R" in the compound (I) is conveniently at a position meta to an oxo group (so that $R_1$ is a group NH—A—N(O)R'R" at the 1-position). However, the compound (I) may contain more than one group NH—A—N(O)R'R", which may be different as regards A and/or R' and R" but which are conveniently identical. Although four or more, particularly three, of such groups may be present, preferred compounds contain two such groups, conveniently with a 1,8, especially a 1,4 and particularly a 1,5 substitution pattern for these groups (so that $R_1$ is a group NH—A—N(O)R'R" at the 1-position together with either $R_2$ being a group NH—A—N(O)R'R" at the 4-position or $R_3$ being a group NH—A—N(O)R'R" at the 5- or 8-position).

The compounds (I) may contain one to three groups NH—A—NHR but conveniently no more than two and preferably no more than one of such groups is present. Where one or more groups NH—A—NHR are present these may differ or not as regards A and/or R between each other and as compared with A and R' and R" in the group(s) NH—A—N(O)R'R" which are present. Preferably, however, each group NH—A—NHR is identical where more than one of these is present. Where only one group NH—A—N(O)R'R" is present or more than one of such groups which are the same are present, a possibility is for any group NH—A—NHR to be the same as the group(s) NH—A—N(O)R'R" as regards A and conveniently for R to be the same as R' and/or R". Where one or more groups NH—A—NHR is present there is preferably one such group at a position meta to an oxo group. Compounds containing such a group are conveniently substituted at one or more of positions 1, 4, 5 and 8 by this group or groups. Preferred compounds of this type contain only one group NH—A—NHR and one group NH—A—N(O)R'R", compounds of particular interest having a group NH—A—N(O)R'R" at position 1 and a group NH—A—NHR at position 8 or especially at position 5 and particularly at position 4, optionally with substitution by a group or groups X, particularly hydroxy, at one or both of the other of these positions.

Conveniently the compounds (I) contain also at least one and preferably two groups X, particularly hydroxy groups. Once again, a group X may be at any of positions 1, 2, 3, 4, 5, 6, 7 and 8 but such a group may conveniently being at one or two of the positions 1, 4, 5 and 8, providing these are not occupied by a group NH—A—NHR or NH—A—N(O)R'R". Conveniently three groups X may be present when only one group NH—A—N(O)R'R" and no group NH—A—NHR is present and two groups X may be present when two groups NH—A—N(O)R'R" or one group NH—A—N(O)R'R" and one group NH—A—NHR are present, such groups X being the same or different. Preferably position 1 is occupied by a group NH—A—N(O)R'R" and the positions 4, 5 and 8 are occupied by a group X, particularly a hydroxy group in each case, or one of these three positions is occupied by another group NH—A—N(O)R'R" or a group NH—A—NHR and the remaining two positions are occupied by a group X, particularly a hydroxy group in each case. Compounds having a group X at each of positions 5 and 8, particularly a hydroxy group in each case, are preferred, for example those indicated under (1), (5) and (7) below.

Compounds of particular interest thus have one of:

(1) $R_1$=NH—A—N(O)R'R" (position 1), $R_2$=H, $R_3$=$R_4$=OH (positions 5 and 8);

(2) $R_1$=NH—A—N(O)R'R" (position 1), $R_2$=OH (position 4), $R_3$=OH (position 5 or position 8), $R_4$=H;

(3) $R_1$=NH—A—N(O)R'R" (position 1), $R_2$=$R_3$=$R_4$=OH (positions 4, 5 and 8);

(4) $R_1$=$R_3$=NH—A—N(O)R'R" (positions 1 and 8, conveniently being identical groups), $R_2$=$R_4$=OH (positions 4 and 5 respectively);

(5) $R_1$=$R_2$=NH—A—N(O)R'R" (positions 1 and 4, conveniently being identical groups), $R_3$=$R_4$=OH (positions 5 and 8); (6) $R_1$=$R_3$=NH—A—N(O)R'R" (positions 1 and 5, conveniently being identical groups), $R_2$=$R_4$=OH (positions 4 and 8);

(7) $R_1$=NH—A—N(O) R'R" at position 1, $R_2$=NH—A—NHR at position 4, $R_3$=$R_4$=OH at positions 5 and 8;

(8) $R_1$=NH—A—N(O)R'R" at position 1, $R_2$=OH at position 4, $R_3$=NH—A—NHR at position 5 and $R_4$=OH at position 8, or (9) $R_1$=NH—A—N(O)R'R" at position 1, $R_2$=$R_3$=OH at positions 4 and 5, and $R_4$=NH—A—HR at position 8. Of these, the compounds of types (1) to (6), particularly of type (5) and especially of type (6) are preferred.

Specific compounds (I) according to the present invention include those compounds of types (1) to (9) just listed in which the or each group NH—A—N(O)R'R" and any group NH—A—NHR has A=$(CH_2)_2$ and R, R' and R" each separately=$CH_3$, $CH_2CH_2CH_3$, $CH_2CH_2OH$, $CH_2CH_2CH_2OH$, $CH(CH_3)CH_2OH$ or $CH_2CHOHCH_2OH$ or particularly $CH_2CH_3$. Preferably R' and R" are identical for each group NH—A—N-

(O)R'R" and conveniently where two groups NH—A—N(O)R'R" are present these are identical. Particularly preferred specific compounds are those of formula (III) and particularly of formula (IV) and their analogues in which the two methyl groups in N(O)(CH₃)₂ are replaced by two n-propyl, 2-hydroxyethyl, 2-hydroxypropyl, 3-hydroxypropyl, 2,3-dihydroxypropyl or particularly ethyl groups, such compounds being in the free base or a salt form.

A further group of specific compounds, which are also of some interest, consists of compounds analogous to compounds (III) and (IV) and the analogues thereof just mentioned but in which the NH—(CH₂)₂—N(O)R'R" group at position 4 or 5 is replaced by a group NH—(CH₂)₂—NHCH₂CH₂OH or a variant of such a group in which the 2-hydroxyethyl group thereof is replaced by a methyl, n-propyl, 2hydroxypropyl, 3-hydroxypropyl, 2,3-dihydroxypropyl or particularly an ethyl group.

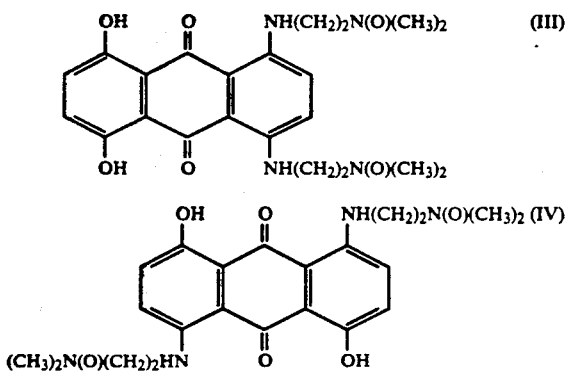

Certain substituents in the compounds (I) may contain one or more asymmetric carbon atoms and the compounds will then exist in stereoisomeric forms. Moreover, in the case where R' and R" are different this will introduce a centre of asymmetry at the nitrogen atom in N-oxide form. It will be appreciated that one stereoisomeric form of a compound may be of particular interest by virtue of advantageous physical properties, for example greater solubility, or biological activity.

As indicated the compounds (I) may be used in the form of a physiologically acceptable salt which will be an acid addition salt with an organic or inorganic acid, for example with one of the acids sulphuric, phosphoric, hydrochloric, hydrobromic, sulphamic, citric, lactic, malic, succinic, tartaric, acetic, benzoic, gluconic and ascorbic. Although the salts will usually have similar physiological properties to the free base they may have the advantage of enhanced solubility, etc.

The compounds (I) may conveniently be prepared through the oxidation of the tertiary amino group(s) of the corresponding compound in which each group NH—A—N(O)R'R" in the compound (I) is in the form NH—A—NR'R". Thus, for example, anthracene-9,10-diones containing various [2-(dialkylamino)ethyl]amino, {2-[di-(hydroxyalkyl)amino]ethyl}amino and [2-(cyclic alkyleneamino)ethyl]amino groups may be oxidized to the ω-N-oxides. Where appropriate the precursor compound which is oxidized may contain one or more modified groups X, R, R' and R" as compared with the parent compound, the groups X, R, R' and R" corresponding to those in the compound (I) being generated after the oxidation has been effected. In particular, it may be appropriate to protect the hydroxy group(s) in groups R, R' and R" which are hydroxyalkyl or dihydroxyalkyl groups or groups X which are hydroxy during the oxidation, for example as an ether group such as benzyloxy, and subsequently regenerate the hydroxy group(s), for example by catalytic reduction of a benzyloxy group. Any suitable oxidizing agent for converting a tertiary aliphatic amine to N-oxide form is suitable, for example hydrogen peroxide, oxone (potassium monopersulphate) and particularly a peracid such as 3-chloroperbenzoic acid. Reaction at room temperature in the dark overnight with an excess of such an acid is usually sufficient to effect conversion to the N-oxide.

Where the compound (I) can exist in d and l forms as well as the dl form an optically active isomer may be synthesised either substantially free from these other forms, or at least in a major proportion by weight as compared with them, either by using optically active reagents in the synthesis of the compound or, particularly in the case of the optically active compounds in which R' and R" are different, by resolving the dl form, especially by using an optically active inorganic or organic acid to provide two stereoisomeric salts with different physical properties. In such an instance and also where the compound (I) is used in the form of a salt the salt may be prepared by reaction of the organic base (I) with the appropriate inorganic or organic acid according to conventional procedures, usually by simple admixture in solution. The acid addition salts are generally crystalline solids which are relatively soluble in water, methanol, ethanol and similar solvents.

Accordingly the present invention comprises a process for the preparation of a compound of formula (I) as defined hereinbefore which comprises oxidizing a compound of formula (Ia)

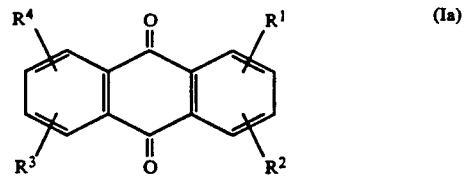

in which R¹, R², R³ and R⁴ correspond to R₁, R₂, R₃ and R₄, respectively, in the compound (I) but with each of the groups of the type NH—A—N(O)R'R" in the compound (I) being instead a group NH—A—NR'R" in the compound (Ia) and one or more groups X, R, R' and R" in the compound (Ia) optionally instead being in a form convertible to said group or groups present in the compound (I), and where appropriate converting the one or more modified groups X, R, R' and R" in the compound (Ia) to the form present in the compound (I) and/or forming an acid addition salt with a physiologically acceptable organic or inorganic acid.

Various routes are available for the synthesis of the intermediates which are oxidized to the compounds (I) of the present invention. One very convenient procedure for the preparation of compounds having a group NH—A—NR'R" at the 1 and 4 positions uses the appropriately substituted 2,3-dihydro(leuco)-1,4-dihydroxyanthracene-9,10-dione which is condensed with the appropriate amine R"R'N—A—NH₂, the 1,4 positions being activated in the leuco compound for reaction with the amine. Such a condensation may conveniently be effected at a temperature in a range of about 25° or 35° to 50° or 60° C. for one or more hours using a solvent such as methanol, ethanol, water, dimethylformamide, 2-methoxyethanol, acetonitrile, nitrobenzene, N,N,N'N'-tetramethylenediamine or mixtures thereof. In some instances a higher temperature and shorter reaction time may be appropriate, for example with the compounds containing cyclic groups NR'R". The leuco derivative is then oxidized to the fully aromatic anthracene-9,10-dione, conveniently using air oxidation or oxidation with hydrogen peroxide, chloranil, sodium perborate or manganese dioxide.

Although leuco compounds are primarily of interest for the preparation of intermediates substituted by two NH—A—NHR'R" groups, it is possible to use them to prepare compounds containing more than two such groups. Thus by using 2,3-dihydro(leuco)-1,4,5,8-tetrahydroxyanthracene-9,10-dione and a large excess of an amine NH—A—NHR'R" an 8-hydroxyanthracene-9,10-dione having three groups NH—A—NHR'R" at the 1,4 and 5 positions may be prepared.

The leuco derivatives themselves are obtainable by heat treatment of the corresponding fully aromatic 1,4-dihydroxyanthracene-9,10-dione, conveniently by heating at above 90° C. for 1 hour or more in a stream of nitrogen and, if necessary, in the presence of a suitable reducing agent such as sodium dithionite or zinc dust. Various anthracene-9,10-diones, particularly hydroxyanthracene-9,10-diones, are commercially available and various syntheses for such compounds are also reported in the literature. One suitable procedure for their preparation involves the reaction of an appropriately substituted phthalic anhydride with hydroquinone in the presence of aluminium chloride and sodium hydroxide at 180° C. for one hour or more. Anthracene-9,10-diones containing one form of substituent X can be modified to provide other forms of substituent X so that, for example, a dione containing an amino group can be treated with sodium hydroxide/dithionite to yield the corresponding hydroxy substituted compound.

Other suitable procedures for the preparation of intermediates for oxidation to the N-oxide include the reaction of the appropriate chloro substituted anthracene-9,10-dione with the appropriate amine R"R'N—A—NH$_2$, for example by heating with a excess of the amine at its reflux temperature for one or more hours. Certain of these chloroanthracene-9,10-diones are known and various syntheses for such compounds are also reported in the literature. Thus, for example, 1,5-dichloro-4,8-dihydroxyanthracene-9,10-dione may be prepared by selective chlorination of 1,4,5,8-tetrahydroxyanthracene-9,10-dione using a stoichiometric amount of sulphuryl chloride and controlled temperature. This precursor may then be used to prepare an intermediate having groups NH—A—NR'R" at the 1 and 5 positions and hydroxy groups at the 4 and 8 positions, the hydroxy groups conveniently being protected during the reaction with the amine R"R'N—A—NH$_2$. A similar approach is suitable for the preparation of other chlorohydroxyanthracene-9,10-dione intermediates.

Where the compound (I) contains one or more groups NH—A—NHR in addition to the one or more groups NH—A—NR'R" the compound may conveniently be produced by reacting a suitable precursor as discussed above with a mixture of amines RN—A—NH$_2$ and R"R'N—A—NH$_2$, the resultant mixture of products then being separated, for example by chromatography. Thus, for example, 2,3-dihydro(leuco)-1,4-dihydroxyanthracene-9,10-dione on reaction with a mixture of 2-(2-hydroxyethylamino)ethylamine and 2-(diethylamino)ethylamine will yield a mixture of 1,4-bis{[2-(diethylamino)ethyl]amino}anthracene-9,10-dione, 1,4-bis{[2-(2-hydroxyethylamino)ethyl]amino}-anthracene-9,10-dione and 1-(2-(diethylamino)ethyl]amino)-4-{[2-(2-hydroxyethylamino)ethyl]amino}anthracene-9,10-dione from which the last mentioned compound may be separated, for example by chromatography. On oxidation, only the tertiary nitrogen atom of the [2-(diethylamino)ethyl)] amino group will be converted to N-oxide form.

Where one or more substituents X is present it may be appropriate, depending on the route of synthesis, to have these present throughout in their final form or to generate the desired groups at a later stage in the synthesis. Ether and ester groups X may of course readily be prepared by modification of hydroxy groups according to known procedures, precursors containing a hydroxy group X more often being described in the literature than those containing a corresponding ether or ester substituent.

It will be appreciated, however, that various alternative methods for the preparation of the compounds (I) and intermediates therefor may be used as will be apparent in particular from the literature relating to such intermediates. Further details of the preparation of intermediates for the preparation of the compounds (I) of the present invention are to be found in U.S. Pat. No. 4,197,249 and U.K. Patent GB 2,004,293B referred to hereinbefore.

Certain of the intermediates corresponding to compounds (I) described herein but without the tertiary amine group(s) in N-oxide form are novel and are within the scope of this invention. Such intermediates include particularly those of formula (Ia) in which at least one of $R_1$ to $R_4$ is a group NH—A—NR'R" and at least one other is a different group NH—A—NR'R" or a group NH—A—NHR.

The compounds (I) may be formulated with a physiologically acceptable diluent or carrier for use as pharmaceuticals for both veterinary, for example in mammals, and particularly human use by a variety of methods. For instance, they may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration may also be used and although compositions for this purpose may incorporate a liquid diluent or carrier, it is more usual to use a solid, for example a conventional solid carrier material such as starch, lactose, dextrin or magnesium stearate. Such solid compositions may take the form of powders but are more conveniently of a formed type, for example as tablets, cachets, or capsules (including spansules). Alternative, more specialized types of formulation include liposomes and nanoparticles.

Other types of administration than by injection or through the oral route which are of use in both human and veterinary contexts include the use of suppositories or pessaries. Another form of pharmaceutical composition is one for buccal or nasal administration or alternatively drops for administration into the eye which may conveniently contain a sterile liquid diluent or carrier.

Other formulations for topical administration include lotions, ointments, creams, gels and sprays.

Compositions may be formulated in unit dosage form, i.e. in the form of discrete portions containing a unit dose or a multiple or sub-unit of a unit dose.

Whilst the dosage of the compound used will vary according to the activity of the particular compound and the condition being treated, it may be stated by way of guidance that a dosage selected in the range from 0.1 to 20 mg/kg per body weight per day, particularly in the range from 0.1 to 5 mg/kg of body weight per day, will often be suitable although higher doses than this, for example in the range from 0.1 to 50 mg/kg of body weight per day (or possibly even as high as described in U.S. Pat. No. 4,197,249) may be considered in view of the lower level of toxic side effects obtained with the compounds (I). This dosage regime may be continued for however many days is appropriate to the patient in question, the daily dosages being divided into several separate administrations if desired. Thus, for example, in the case of conditions such as advanced breast cancer, non-Hodgkin's lymphyoma and hepatoma, treatment for one day followed by a repeated dose after an interval, such as 21 days, may be appropriate whilst for the treatment of acute non-lymphocytic leukaemia, treatment over 5 consecutive days may be more suitable.

The compounds (I) are of particular value for the treatment of cancer in warm blooded animals including humans. The compounds are of interest in relation to the treatment of solid tumours, such as various forms of sarcoma and carcinoma, and also for disseminated tumours such as leukaemias. Areas of particular interest are the treatment of non-Hodgkins lymphoma, of breast cancer, and of acute non-lymphocytic leukaemia. In the treatment of cancer parenteral and sometimes topical administration is often of particular interest. Moreover, it may be advantageous to use the compounds (I) in a combined treatment, given separately or together in the same composition, with other anti-cancer agents, such as mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

In a variation of the usual procedure which relies upon the anaerobic conditions within neoplastic tissue to effect selective reduction of the N-oxide in such tissue, the selectivity as between neoplastic and normal tissue can be enhanced. Thus antibodies can be raised against tumours by conventional procedures, particularly using hybridoma technology, and linked covalently to a reductase using one of various conventional linking agents. The conjugate is administered to the patient when it localises in the body at the tumour site and the compound (I) is then administered, the action of the reductase enhancing the specificity of the action of the compound at the tumour site.

The present invention thus includes a method of aiding regression and palliation of a cancer sensitive to treatment with a compound of formula which comprises administering to a patient a therapeutically effective amount of a compound (I) as defined hereinbefore.

In addition to their anti-cancer use the compounds (I) are of interest for various other pharmaceutical applications in view of their activity as chelating agents.

The invention is illustrated by the following Examples.

EXAMPLES

Example 1

Preparation of 1,5-bis-{[2-(diethylamino-N-oxide)ethyl]amino}anthracene-9,10-dione (1)

1,5-bis-{[2-(diethylamino)ethyl]amino}anthracene-9,10-dione

A solution of 5.52 g (0.02 mol) of 1,5-dichloroanthracene-9,10-dione in 23.2 g (0.2 mol) of 2-(diethylamino)ethylamine is heated at reflux temperature for 4 hours. The mixture is cooled in an ice-bath and 100 ml concentrated hydrochloric acid is added with stirring. This acidic mixture is extracted with three aliquots of 200 ml of diethylether followed by three aliquots of 200 ml of chloroform. The aqueous layer is collected and made alkaline with sodium hydroxide solution, extracted into chloroform and evaporated in vacuo at 30° C. The oily residue is washed with water, dissolved in methanol and titrated with hydrogen chloride in dry diethyl ether to give a precipitate which is dried to yield 5.2 g of the title compound as the hydrochloride in the form of a dark red solid, m.p. 158.5°–159.5° C.; $\lambda_{max}$(deionised water) (E/cm/M) 231 nm (34280), 516 nm (10690).

(2)

1,5-bis-{[2-(diethylamino-N-oxide)ethyl]amino}anthracene-9,10-dione

A solution of 1.25 g (0.004 mol) of 1,5-{2-(diethylamino)-ethyl]amino}anthracene-9,10-dione free base (prepared by washing the oily residue of (1) with water and drying) in 20 ml of chloroform is cooled in an ice bath while stirring. This solution is treated with 1.2 g of 3-chloroperbenzoic acid, allowed to come to room temperature and left for 18 hours protected from light. The mixture is evaporated in vacuo to a small volume and is subject to flash chromatography using a column of 70–230 mesh (60 A) silica gel and an eluting solvent of chloroform:methanol (5:1 v/v) to yield 0.45 g of the title compound. m.p. (following recrystallisation from chloroform to give dark red crystals) 125°–129° C. (decomposition): $\lambda_{max}$(deionised water) (E/cm/M) 231 nm (44030), 516 nm (11330).

EXAMPLE 2

Preparation of 1,4-bis-{[2-(diethylamino-N-oxide)ethyl]amino}-anthracene-9,10-dione (1) 1,4-bis-{[2-(diethylamino)ethyl]amino}anthracene-9,10-dione A mixture of 5 g (0.021 mol) of 1,4-dihydroxyanthracene-9,10-dione and 2 g (0.014 mol) of sodium dithionite in 20 ml water is stirred whilst heating under nitrogen at 90° C. until the mixture turns from orange to brown indicating the presence of 2,3-dihydro(leuco)-1,4-dihydroxyanthracene-9,10-dione. To this reaction mixture is added dropwise 20 g (0.17 mol) of 2-(diethylamino)-ethylamine over a 30 minute period. The mixture is heated at 50°–55° C. for 2 hours and 20 ml of ethanol are added. The solution is then aerated and 200 ml of 2M hydrochloric acid are added. The acidic mixture is washed with 3×200 ml of diethylether followed by 3×200 ml of chloroform. The aqueous phase is made alkaline by the addition of sodium hydroxide solution and extracted with 3×200 ml chloroform. The mixture is evaporated in vacuo to a 5 ml volume and subjected to flash chromatography using a column of 70–230 mesh (60 A) silica gel ($SiO_2$) and an eluting solvent of chloroform followed by chloroform:methanol (1:1 v/v). The blue black material removed from the column in chloroform/methanol is evaporated in vacuo to yield 0.7 g of the title compound, m.p. 107.5°–108.5° C.; $\lambda_{max}$ $\lambda_{max}$ (deionised water) (E/cm/M) 256 nm (50950), 584 nm (18650).

(2)

1,4-bis-{2-(diethylamino-N-oxide)ethyl]amino}anthracene-9,10-diethylamino)ethyl-aminolanthracene-9,10-dione in 15 ml of dry chloroform is added 1.5 g (0.008 mol) of 3-chloroperbenzoic acid. The mixture is stirred for 30 minutes, allowed to come to rom temperature and the left for 18 hours protected from light. The mixture is evaporated in vacuo to a 5 ml volume and subjected to reverse phase chromatography using as column of octadecylsilane bonded to silica gel, 10 μM particle size, and methanol:ammonium formate, 0.5M, pH 4.25 (30:70 v/v), as an eluting solvent. The eluate fractions identified by thin-layer chromatography (chloroform/methanol 1:1 v/v) to contain a single dark blue-coloured component are pooled, extracted with chloroform and evaporated in vacuo. Drying over phosphorus pentoxide yields 0.17 g of the title compound as a dark blue solid, m.p. 115°–118° C. (decomposition): $\lambda_{max}$ (deionised water) (E/cm/M) 256 nm (20900), 584 nm (5880).

Example 3

Preparation of
1-{[2-(diethylamino-N-oxide)ethyl]amino}anthracene-9,10-dione (1)

1-{2-(diethylamino)ethyl]amino}anthracene-9,10-dione

A mixture of 12.1 g (0.05 mol) of 1-chloroanthraquinone and 58 g (0.5 mol) of 2-(diethylamino)ethylamine is heated under reflux for 2 hours. The reaction product is worked up as described in Example 1 except that the oily residue is only washed with water and then dried to yield 3.24 g of the title compound as the free base in the form of an orange-red solid, m.p. 98° C.; $\lambda_{max}$(deionised water) (E/cm/M) 248 nm (27180), 493 nm (5770).

(2)

1-{[2-(diethylamino-N-oxide)ethyl]amino}anthracene-9,10-dione 1.25 g (0.0039 mol) of 1-{[2-(diethylamino)ethyl]amino}anthracene-9,10-dione and 1.2 g (0.0068M) 3-chloroperbenzoic acid are reacted for 18 hours as described in Example 1. Silica gel flash chromatography as in Example 1 but with chloroform/methanol (1:5 v/v) as eluting solvent gives an eluate which is evaporated in vacuo. Recrystallisation of the residue from chloroform yields 0.45 g of the title compound as an orange-red solid, m.p. 120°–125° C. (decomposition); $\lambda_{max}$ (deionised water) (E/cm/M) 248 nm (32330), 493 nm (6180).

Example 4

Preparation of
1,8-bis-{[2-(diethylamino-N-oxide)ethyl]amino}anthracene-9,10-dione (1)

1,8-bis-{(2-(diethylamino)ethyl]amino}anthracene-9,10-dione

A mixture of 5.52 g (0.02 mol) of 1,8-dichloroanthraquinone and 23.2 g (0.2M) 2-(diethylamino)ethylamine is heated under reflux for 3 hours. The reaction product is washed up as described in Example 1 except that the oily residue is only washed with water and then dried to yield 3.63 g of the title compound as the free base in the form of a purple solid, m.p. 103.5°–106.5° C.; $\lambda_{max}$ (deionised water) (E/cm/M) 236 nm (54940), 542 nm (13200).

(2)

1,8-bis-{[2-(diethylamino-N-oxide)ethyl]amino}anthracene-9,10-dione 1.25 g (0.003 mol) of 1,8-{[2-(diethylamino)ethyl]amino}-anthracene-9,10-dione and 2.5 g (0.0135 mol) 3-chloroperbenzoic acid are reacted for 4 hours as described in Example 1. Flash chromatography as in Example 1 but using chloroform/methanol (1:1 v/v) eluting solvent gives an eluate which is evaporated in vacuo. Recrystallisation of the residue from chloroform yields 0.18 g of the title compound as a purple solid m.p. 118°–119° C. (decomposition): $\lambda_{max}$ (deionised water) (E/cm/M) 236 nm (39530), 542 nm (8360).

Example 5

Preparation of
1,4-bis-{[2-(diethylamino-N-oxide)ethyl]amino}-5,8-dihydroxyanthracene-9,10-dione (1)

1,4-bis-{[2-(diethylamino)ethyl]amino)-5,8-dihydroxyanthracene-9,10-dione

A mixture of 1.0 g (0.0037 mol) of leuco-1,4,5,8-tetrahydroxyanthraquinone and 5 g (0.043 mol) of N,N-diethylaminoethylamine in methanol is heated for 10 minutes to reflux temperature. The ethanol and unreacted N,N-diethylaminoethylamine are removed by distillation in vacuo and the remaining solid recrystallised from ethyl acetate to yield 0.64 g of the title compound as a dark blue solid, m.p. 203° C. as the dihydrochloride salt; $\lambda_{max}$ (distilled water) (E/cm/M) 239 nm (44910), 605 nm (10890), 659 nm (10710).

(2)

1,4-bis-{[2-(diethylamino-N-oxide)ethyl]amino}-5,8-dihydroxyanthracene-9,10-dione 0.108 g (0.00023 mol) of 1,4-bis-{[2-(diethylamino)ethyl]amino}-5,8-dihydroxyanthracene-9,10-dione is dissolved in 5 ml dichloromethane and the solution is cooled in an ice-bath whilst stirring. The solution is treated with 0.2 g (0.000115 mol) of 3-chloroperbenzoic acid, allowed to come to room temperature and left for 18 hours protected from light. The mixture is then subjected to flash column chromatography using a column of silica gel (60A) and a step-gradient eluting solvent of dichloromethane:methanol:triethylamine starting with dichloromethane:triethylamine (99:1 v/v) followed by dichloromethane:methanol:triethylamine (90:9:1 v/v/v) then dichloromethane:methanol:triethylamine (49.5:49.5:1 v/v/v) and finally methanol:triethylamine (99:1 v/v). The major eluting blue fraction is collected, filtered and evaporated in vacuo to yield 0.08 g of the title compound as a dark blue solid, m.p. 155°–158° C. (decomposition); $\lambda_{max}$ (distilled water) (E/cm/M) 240 nm (15690), 609 nm (8809), 662 nm (5750).

Example 6

Preparation of 1,4-bis-{[2-(dimethylamino-N-oxide)ethyl]amino}-5,8-dihydroxyanthracene-9,10-dione (1)

1,4-bis-{[2-(dimethylamino)ethyl]amino}-5,8-dihydroxyanthracene-9,10-dione

A solution of 1.0 g (0.0037 mol) of leuco-1,4,5,8-tetrahydroxyanthraquinone in methanol is refluxed under nitrogen. To this is slowly added 2 g (0.023 mol) of N,N-dimethylaminoethylamine and the mixture is stirred at 50° C. for 1 hour. The mixture is then stirred for 16 hours in air. The ethanol and unreacted N,N-dimethylaminoethyl amine are removed by distillation in vacuo and the remaining solid is recrystallised from ethyl acetate/methanol (2:1 v/v) to yield 0.68 g of the title compound as a dark blue solid, m.p. 199°–200.5° C. as the dihydrochloride salt, $\lambda_{max}$ (distilled water) (E/cm/M) 242 nm (43270), 606 nm (18050), 658 nm (16220).

(2)

1,4-bis-{[2-(dimethylamino-N-oxide)ethyl]amino}-5,8-dihydroxyanthracene-9,10-dione A solution of 0.10 g (0.000242 mol) of 1,4-bis-{[2-(dimethylamino)ethyl]amino}-5,8-dihydroxyanthracene-9,10-dione in 5 ml dichloromethane is cooled in an ice-bath whilst stirring. To this solution is added 0.2 g (0.000115 mol) of 3-chloroperbenzoic acid and the product is allowed to come to room temperature and left for 8 hours protected from light. The mixture is then subjected to flash column chromatography using a column of silica gel (60A) and a step-gradient eluting solvent of dichloromethane:methanol:triethylamine starting with dichloromethane:methanol (50:50 v/v) followed by dichloromethane:methanol (20:80 v/v) and finally methanol:triethylamine (99:1 v/v). The last eluting blue fraction is collected, filtered and evaporated in vacuo to yield 0.075 g of the title compound as a dark blue solid, m.p. 124°–128° C. (decomposition); $\lambda_{max}$ (distilled water) (E/cm/M) 222 nm (15500), 612 nm (6110), 664 nm (3685).

Example 7

Preparation of 1,4-bis-{[2-(diethylamino-N-oxide)propyl]amino}-5,8-dihydroxyanthracene-9,10-dione (1)

1,4-bis-{[2-(diethylamino)propyl]amino}-5,8-dihydroxyanthracene-9,10-dione

A mixture of 1.0 g (0.0037 mol) of leuco-1,4,5,8-tetrahydroxyanthraquinone in 20 ml of aqueous potassium carbonate (5% w/v) and 0.2 g of sodium dithionite is stirred and flushed with nitrogen. The mixture is then treated with 4 g (0.003 mol) of N,N-diethylaminopropylamine and stirred at 80° C. for 18 hours in air. The ethanol and unreacted N,N-diethylaminopropylamine are removed by distillation in vacuo and the remaining solid is recrystallised from ethyl acetate to yield 0.8 g of the title compound as a dark blue solid, m.p. 126°–128° C.; $\lambda_{max}$ (distilled water) (E/cm/M) 241 nm (15370), 611 nm (12460), 668 nm (11280).

(2)

1,4-bis-{[2-(diethylamino-N-oxide)propyl]amino}-5,8-dihydroxyanthracene-9,10-dione A solution of 0.10 g (0.000242 mol) of 1,4-bis-{[2-(diethylamino)propyl]amino}-5,8-dihydroxyanthracene-9,10-dione is dissolved in 5 ml dichloromethane and cooled in an ice-bath whilst stirring. The solution is treated with 0.2 g (0.000115 mol) of 3-chloroperbenzoic acid, allowed to come to room temperature and left for 8 hours protected from light. The mixture is then subjected to flash column chromatography using a column of silica gel (60A) and a step-gradient eluting solvent of dichloromethane:methanol:triethylamine starting with dichloromethane:methanol (50:50 v/v) followed by dichloromethane:methanol (20:80 v/v) and finally methanol:triethylamine (99:1 v/v). The last eluting blue fraction is collected, filtered and evaporated in vacuo to yield 0.8 g of the title compound as a dark blue solid which remains as a solid in a dessicator but becomes sticky on attempting a melting point determination; $\lambda_{max}$ (distilled water) (E/cm/M) 248 nm (14220), 614 nm (8600), 666 nm (5144).

Example 8

Preparation of 1-{[2-(diethylamino-N-oxide)ethyl]amino}-4-{[2-[(2-hydroxyethyl)amino]ethyl]amino}-5,8-dihydroxyanthracene-9,10-dione (1)

1-{[2-(diethylamino)ethyl]amino}-4-{[2-[(2-hydroxyethyl)-amino]ethyl]amino}-5,8-dihydroxyanthracene-9,10-dione A solution of 1.0 g (0.0037 mol) of leuco-1,4,5,8-tetrahydroxyanthraquinone in 10 ml ethanol is heated at 50° C. under nitrogen with 2.1 g (0.00184 mol) of N,N-diethylaminoethylamine and 1.9 g (0.00184 mol) of 2-hydroxyethylaminoethylamine for 6 hours and then stirred in air for 16 hours. The ethanol and unreacted N,N-diethylaminoethylamine and 2-hydroxyethylaminoethylamine are removed by distillation in vacuo. The remaining solid is dissolved in dichloromethane:methanol:0.3% w/v aqueous ammonia (96:3:1 v/v/v) and subjected to flash chromatography using silica gel (60A) and dichloromethane:methanol:aqueous ammonia (96:3:1 v/v/v) as eluting solvent. The major eluting fraction is evaporated in vacuo and the solid again column chromatographed on silica gel (60A) using a step gradient of dichloromethane:methanol (50:50 v/v) followed by dichloromethane:methanol:aqueous ammonia (49.75:49.75:0.5 v/v/v). The major eluting blue fraction is collected, filtered and evaporated in vacuo to yield 0.2 g of the title compound as a dark blue solid, m.p. 165°–167° C.; $\lambda_{max}$ (distilled water) (E/cm/M) 232 nm (3380), 608 nm (20782), 660 nm (18900).

(2)

1-{[2-(diethylamino-N-oxide)ethyl]amino}-4-{[2-[(2-hydroxyethyl)amino]ethyl]amino}-5,8-dihydroxyanthracene-9,10-dione A solution of 0.10 g (0.00023 mol) of 1-{[2-(diethylamino)-ethyl]amino}-4-{[2-[(2-hydroxyethyl)amino]ethyl]amino}-5,8-dihydroxyanthracene-9,10- dione is dissolved in 5 ml dichloromethane and cooled in an ice-bath whilst stirring. This solution is treated with 0.1 g (0.000058 mol) of 3-chloroperbenzoic acid, allowed to come to room temperature and left for 18 hours protected from light. The mixture is then subjected to flash column chromatography using a column of silica gel (60A) and a step-gradient eluting solvent as described for Example 6. The last eluting blue fraction is collected, filtered and evaporated in vacuo to yield 0.06 g of the title compound as a dark blue solid, m.p. 92°–93.5° C. (decomposition); $\lambda_{max}$ (phosphate buffer pH 7.4) (E/cm/M) 238 nm (8203), 607 nm (6396), 658 nm (4733).

Example 9

Preparation of
1-{[2-(diethylamino-N-oxide)ethyl]amino}-4-{[2-(ethylamino)ethyl]amino}-5,8-dihydroxyanthracene-9,10-dione

1)

1-{([2-(diethylamino)ethyl]amino}-4-{[2-(ethylamino)ethyl]-amino}-5,8-dihydroxyanthracene-9,10-dione A suspension of 1.0 g (0.0037 mol) of leuco-1,4,5,8-tetrahydroxyanthraquinone in 10 ml of propan-2-ol is stirred at 50° C. under nitrogen. To the mixture is added 2.1 g (0.00184 mol) of N,N-diethylaminoethylamine and 1.6 g (0.00184 mol) of N-ethylaminoethylamine the product is stirred in for 12 hours under nitrogen and then for a further 6 hours in air. The ethanol and unreacted N,N-diethylaminoethylamine and N-ethylaminoethylamine are removed by distillation in vacuo and the remaining solid is recrystallised from ethyl acetate to yield 0.2 g of the title compound as a dark blue solid m.p. 161°–163° C.; $\lambda_{max}$ (distilled water) (E/cm/M) 242 nm (15520), 609 nm (10196), 659 nm (12640).

(2)

1-{[2-(diethylamino-N-oxide)ethyl]amino}-4-{[2-(ethylamino)-ethyl]amino}-5,8-dihydroxyanthracene-9,10-dione 0.10 g (0.00023 mol) of 1-{[2-(diethylamino)ethyl]amino}-4-{[2-(ethylamino)ethyl]amino}-5,8-dihydroxyanthracene-9,10-dione is dissolved in 5 ml dichloromethane and the solution is cooled in an ice-bath whilst stirring. To the solution is added 0.1 g (0.000058 mol) of 3-chloroperbenzoic acid and it is then allowed to come to room temperature and left for 16 hours protected from light. The mixture is then subjected to flash column chromatography using a column of silica gel (60A) and a step-gradient eluting solvent of dichloromethane:-methanol (90:10 v/v) followed by dichloromethane:methanol:0.3% w/v aqueous ammonia (90:9:1 v/v/v). The last eluting blue fraction is collected, filtered and evaporated in vacuo to yield 0.08 g of the title compound as a dark blue solid, which remains as a solid in a dessicator but becomes sticky on attempting a melting point determination; $\lambda_{max}$ (distilled water) (E/cm/M) 244nm (14776), 612 nm (10080), 662 nm (6532).

Example 10

Preparation of
1,4-bis-{[2-(di(2-hydroxyethyl)amino)-N-oxide ethyl]amino}-5,8-dihydroxyanthracene-9,10-dione.

(1)

1,4-bis-{[2-(di(2-hydroxyethyl)amino)ethyl]amino}-5,8-dihydroxyanthracene-9,10-dione A mixture of 1.0 g (0.0037 mol) of leuco-1,4,5,8-tetrahydroxyanthraquinone and 4 g (0.003 mol) of N,N-di(2-hydroxyethyl)aminoethylamine treated as described in Example 7 produces a dark solid. This is dissolved in 10 ml of methanol:dichloromethane (50:50 v/v) subjected to silica gel (60A) flash chromatography using a step gradient of dichloromethane:methanol (90:10 v/v) followed by dichloromethane:methanol (50:50 v/v). The major eluting fraction is collected, filtered and evaporated in vacuo to yield the title compound as a dark blue solid, which remains as a solid in a dessicator but becomes sticky on attempting a melting point determination; $\lambda_{max}$ (distilled water) (E/cm/M) 235 nm (12726), 605 nm (7236), 655 nm (6396).

(2)

1,4-bis-{[2-(di(2-hydroxyethyl)amino)ethyl]amino}-5,8-dihydroxyanthracene-9,10-dione 0.09 g (0.00017 mol) of 1,4-bis-{[2-(di(2-hydroxyethyl)ethyl]-amino}-5,8-dihydroxyanthracene-9,10-dione is dissolved in 5 ml dichloromethane and the solution is cooled in an ice-bath whilst stirring. To the solution is added 0.1 g (0.00044 mol) of 3-chloroperbenzoic acid and it is then allowed to come to room temperature and left for 16 hours protected from light. The reaction mixture is filtered and the solid washed five times with 25 ml aliquots of dichloromethane followed five times by 10 ml aliquots of methanol. The residue is filtered to yield 0.03 g of the title compound as a dark blue solid, m.p. 134.5°–135.5° C.; $\lambda_{max}$ (distilled water) (E/cm/M) 238 nm (24527), 610 nm (9331), 666 nm (5435).

Example 11

Preparation of
1-{[2-(dimethylamino-N-oxide)ethyl]amino}-4-{[2-[2-hydroxyethyl)amino]ethyl]amino}-5,8-dihydroxyanthracene-9,10-dione (1)

1-{[2-(dimethylamino)ethyl]amino}-4-{[2-[2-hydroxyethyl)amino]ethyl]amino}-5,8-dihydroxyanthracene-9,10-dione A mixture of 1.0 g (0.0037 mol) of leuco-1,4,5,8-tetrahydroxyanthraquinone, 1.6 g (0.00184 mol) of N,N-dimethylaminoethylamine and 1.9 g(0.00184 mol) of 2-hydroxyethylaminoethylamine in ethanol is stirred under nitrogen at room temperature for 3 hours. The mixture is then stirred for 16 hours in air. The ethanol and unreacted N,N-dimethylaminoethylamine and 2-hydroxyethylaminoethylamine are removed by distillation in vacuo. The resulting solid is dissolved in dichloromethane:methanol:0.3% w/v aqueous ammonia (49.75:49.75:0.5 v/v/v) and subjected to column chromatography on silica gel (60A). The chromatography procedure is repeated using dichloromethane:methanol:triethylamine (90:9:1 v/v/v) and the major eluting fraction is collected, filtered and evaporated in vacuo to yield 0.260 g of the title compound as a dark blue solid, m.p. 136°-140° C. as the dihydrochloride; λ_max (distilled water) (E/cm/M) 244nm (30430), 607nm (15683), 658nm (13560).

(2)
1-{[2-(dimethylamino-N-oxide)ethyl]amino}-4-{[2-[2-hydroxyethyl)amino]ethyl]amino}-5,8-dihydroxyanthracene-9,10-dione 0.10 g (0.00023 mol) of 1-{[2-(dimethylamino)ethyl]amino}-4-{[2-[(2-hydroxyethyl)amino]ethyl]amino}-5,8-dihydroxyanthracene-9,10-dione is dissolved in 5 ml of dichloromethane and the solution is cooled in an ice-bath whilst stirring. To this solution is added 0.1 g (0.000058 mol) of 3-chloroperbenzoic acid and it is then allowed to come to room temperature and left for 18 hours protected from light. The mixture is then treated as described in Example 8 to yield 0.03 g of the title compound as a dark blue solid, m.p. 128°-132° C. (decomposition); λ_max (phosphate buffer pH 7.4) (E/cm/M) 240 nm(13243), 610 nm(6475), 664 nm(5915).

Example 12: Biological Activity

The cytotoxicity was compared of the four compounds
(a) 1,8-bis-{[2-(diethylamino-N-oxide)ethyl]amino}anthracene-9,10-dione
(b) 1,4-bis-{[2-(diethylamino-N-oxide)ethyl]amino}anthracene-9,10-dione,
(c) 1-{[2-(diethylamino-N-oxide)ethyl]amino}anthracene-9,10-dione, and
(d) 1,5-bis-{[2-(diethylamino-N-oxide)ethyl]amino}anthracene-9,10-dione,
under aerobic and anaerobic conditions and a comparison was also made with the cytotoxicity of the corresponding compound in which the terminal, tertiary nitrogen atom is not in N-oxide form.

Cells of the MCF-7 human breast cancer cell line (5×10^5/ml) were seeded into 12-well culture plates containing RPMI 1640 medium (Flow Labs., Irving, Scotland) supplemented with 10% v/v foetal bovine serum and grown at 37° C. to confluence. In the aerobic experiments, the cells were treated with one of a range of concentrations of the compound and then incubated in air for 24 hours. In the anaerobic experiments, following treatment of the cells with compound the culture plates were placed in a gas-tight chamber (Flow Labs) which was flushed with nitrogen 30 minutes, the cells then being incubated for 24 hours under nitrogen. Following both types of experiment the cells were washed free of the compound with isotonic saline and were then grown for a further 3 days in air. The surviving monolayer cells were counted using a Coulter counter.

The results obtained are presented in the Figure, the different parts (a) to (d) of which correspond to the four compounds identified above by these letters. In each part of the Figure plot 1 corresponds to the N-oxide under aerobic conditions, plot 2 corresponds to the N-oxide under anaerobic conditions and plot 3 corresponds to the corresponding tertiary amine under anaerobic conditions.

The Figure shows that each of the N-oxides is substantially non-cytotoxic in air but these compounds are cytotoxic when cells are exposed to them in nitrogen, although the level of cell kill observed is not necessarily fully equivalent to the level resulting from the use of an equimolar amount of the parent tertiary amines under the same conditions.

I claim:
1. A compound of formula (I)

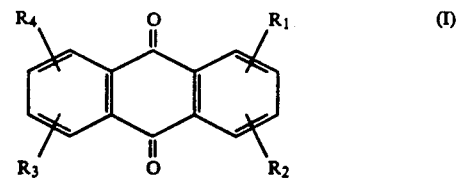

in which $R_1$, $R_2$, $R_3$ and $R_4$ are each separately selected from the group consisting of hydrogen, X, NH—A—NHR and NH—A—N(O)R'R" wherein X is hydroxy, halogeno, amino, $C_{1-4}$ alkoxy or $C_{2-8}$ alkanoyloxy, A is a $C_{2-4}$ alkylene group with a chain length between NH and NHR or N(O)R'R" of at least 2 carbon atoms and R, R' and R" are each separately selected from the group consisting of $C_{1-4}$ alkyl groups and $C_{2-4}$ hydroxyalkyl and $C_{2-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, but with the proviso that at least one of $R_1$ to $R_4$ is a group NH—A—N(O)R'R", the compound optionally being in the form of a physiologically acceptable salt.

2. A compound according to claim 1, in which $R_1$, $R_2$, $R_3$ and $R_4$ are each separately selected from the group consisting of hydrogen, hydroxy, NH—A—NHR and NH—A—N(O)R'R".

3. A compound according to claim 1 or 2, in which A is ethylene.

4. A compound according to claim 1, 2 or 3, in which R, R' and R" are each separately selected from the group consisting of $CH_3$, $CH_2CH_3$, $CH_2CH_2CH_3$, $CH_2CH_2OH$, $CH_2CH_2CH_2OH$, $CH(CH_3)CH_2OH$ and $CH_2CHOHCH_2OH$.

5. A compound according to claim 1, which contains one or two groups NH—A—N(O)R'R", these being separately selected from NH—$(CH_2)_2$—N(O)$(CH_3)_2$, NH—$(CH_2)_2$-N(O)$(CH_3)C_2H_5$, NH—$(CH_2)_2$—N(O)$(C_2H_5)_2$, NH—$(CH_2)_2$—N(O)$(CH_2CH_2OH)_2$, NH—$(CH_2)_2$—N(O)$(CH_2CH_2CH_2OH)_2$, NH—$(CH_2)_2$—N(O)CH$(CH_3)$OH and NH—$(CH_2)_2$—N(O)$(CH_2CHOHCH_2OH)_2$.

6. A compound according to claim 1, which contains one group NH—A—N(O)R'R" and one group NH—A—NHR, this latter group being selected from the group consisting of NH—$(CH_2)_2$—NHCH$_3$, NH—$(CH_2)_2$—NHC$_2$H$_5$, NH—$(CH_2)_2$—NHCH$_2$CH$_2$OH, NH—$(CH_2)_2$—NHCH$_2$CH$_2$CH$_2$OH, NH—$(CH_2)_2$—NHCH$(CH_3)$CH$_2$OH and NH—$(CH_2)_2$—NHCH$_2$CHOHCH$_2$OH.

7. A compound according claim 1, in which
(1) $R_1$=NH—A—N(O)R'R" at position 1, $R_2$=H, $R_3$=$R_4$=OH at positions 5 and 8;
(2) $R_1$=NH—A—N(O)R'R" at position 1, $R_2$=OH at position 4, $R_3$=OH at position 5 or position 8 and $R_4$=H;
(3) $R_1$=NH—A—N(O)R'R" at position 1 and $R_2$=$R_3$=$R_4$=OH at positions 4, 5 and 8;
(4) $R_1$=$R_3$=NH—A—N(O)R'R" at positions 1 and 8 and $R_2$=$R_4$=OH at positions 4 and 5;
(5) $R_1$=$R_2$=NH—A—N(O)R'R" at positions 1 and 4 and $R_3$=$R_4$=OH at positions 5 and 8; or (6) $R_1=R_3=NH-A-N(O)R'R''$ at positions 1 and 5 and $R_2=R_4=OH$ at positions 4 and 8.

8. A compound according to claim 6, in which
(1) $R_1=NH-A-N(O)R'R''$ at position 1, $R_2=NH-A-NHR$ at position 4, and $R_3=R_4=OH$ at positions 5 and 8;
(2) $R_1=NH-A-N(O)R'R''$ at position 1, $R_2=OH$ at position 4, $R_3=NH-A-NHR$ at position 5 and $R_4=OH$ at position 8, or
(3) $R_1=NH-A-N(O)R'R''$ at position 1, $R_2=R_3=OH$ at positions 4 and 5 and $R_4=NH-A-NHR$ at position 8.

9. A compound according to claim 1, in which $R_1=R_2=NH-A-N(O)R'R''$ at positions 1 and 4 and $R_3=R_4=OH$ at positions 5 and 8, or $R_1=R_3=NH-A-N(O)R'R''$ at positions 1 and 5 and $R_2=R_4=OH$ at positions 4 and 8 with both $NH-A-N(O)R'R''$ being $NH-(CH_2)_2N(O)(CH_3)_2$ or $NH-(CH_2)_2N(O)(CH_2CH_2O)_2$.

10. A compound according to claim 1, in which $R_1=NH-A-N(O)R'R''$ at position 1, $R_2=NH-A-NHR$ at position 4 and $R_3=R_4=OH$ at positions 5 and 8 or $R_1=NH-A-N(O)R'R''$ at position 1, $R_2=OH$ at position 4, $R_3=NH-A-NHR$ at position 5 and $R_4=OH$ at position 8 with $NH-A-N(O)R'R''$ being $NH-(CH_2)_2N(O)(CH_3)_2$ or $NH-(CH_2)_2N(O)(CH_2CH_2OH)_2$ and $NH-A-NHR$ being $NH-(CH_2)_2NHCH_3$ or $NH(CH_2)_2NHCH_2CH_2OH$.

11. A pharmaceutical composition comprising a compound of formula (I) as defined in claim 1 together with a physiologically acceptable diluent or carrier.

12. A method of aiding regression and palliation of a cancer which comprises administering to a patient a therapeutically effective amount of a compound of formula (I) as defined in claim 1.

13. A compound according to claim 1, which is 1,4-bis-{[2-(diethylamino-N-oxide)ethyl]amino}-5,8-dihydroxy anthracene-9,10-dione.

* * * * *

UNITED STATES PATENT AND TRADEMARK OFFICE
CERTIFICATE OF CORRECTION

PATENT NO. : 5,132,327
DATED : July 21, 1992
INVENTOR(S) : L. H. Patterson It is certified that error appears in the above-identified patent and that said Letters Patent is hereby corrected as shown below:

Column 18 lines 46-47 delete ", $NH-(CH_2)_2-N(O)CH(CH_3)OH$"

Column 19 line 20 delete "$NH-(CH_2)_2N(O)(CH_2CH_2O)_2$" and replace by --$NH-(CH_2)_2N(O)(CH_2CH_2OH)_2$"--

Column 20 lines 2-3 delete "$R_2-NH-A-NHR$" and replace by replace by --$R_2 = NH-A-NHR$--

Signed and Sealed this

Twelfth Day of October, 1993

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,132,327
DATED : July 21, 1992
INVENTOR(S) : L. H. Patterson It is certified that error appears in the above-identified patent and that said Letters Patent is hereby corrected as shown below:

Column 18 line 43 insert --the group consisting of-- after "from"

Column 20 line 14 insert --sensitive to treatment with a compound of formula (I),-- after "cancer"

Signed and Sealed this

Fourteenth Day of December, 1993

Attest:

BRUCE LEHMAN

*Attesting Officer*     *Commissioner of Patents and Trademarks*